(12) United States Patent
Jansma et al.

(10) Patent No.: US 10,144,728 B2
(45) Date of Patent: Dec. 4, 2018

(54) ALKYLATION OF PICOLINAMIDES WITH SUBSTITUTED CHLOROACYLALS UTILIZING A CROWN ETHER CATALYST

(71) Applicant: DOW AGROSCIENCES LLC, Indianapolis, IN (US)

(72) Inventors: Matthew J. Jansma, Midland, MI (US); Timothy J. Adaway, Midland, MI (US); Michael Lee Trippeer, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/283,479

(22) Filed: Oct. 3, 2016

(65) Prior Publication Data

US 2017/0096414 A1    Apr. 6, 2017

Related U.S. Application Data

(60) Provisional application No. 62/237,844, filed on Oct. 6, 2015.

(51) Int. Cl.
*C07D 405/12* (2006.01)
*B01J 27/08* (2006.01)
*B01J 31/02* (2006.01)
*B01J 31/26* (2006.01)

(52) U.S. Cl.
CPC ............ *C07D 405/12* (2013.01); *B01J 27/08* (2013.01); *B01J 31/0204* (2013.01); *B01J 31/26* (2013.01); *B01J 2231/44* (2013.01); *B01J 2531/007* (2013.01)

(58) Field of Classification Search
CPC .................................................... C07D 405/12
USPC ........................................ 546/281.7; 514/336
See application file for complete search history.

(56) References Cited

U.S. PATENT DOCUMENTS

| 6,861,930 B2 | 3/2005 | Meyer et al. |
| 7,091,270 B2 | 8/2006 | Zilberman et al. |
| 9,131,690 B2 * | 9/2015 | Meyer .................... A01N 43/40 |
| 2013/0060023 A1 | 3/2013 | Bronk et al. |

FOREIGN PATENT DOCUMENTS

EP    0490515 B1    10/1997

OTHER PUBLICATIONS

Dorwald, Side Reactions in Organic Synthesis, 2005, Wiley: VCH Weinheim Preface, pp. 1-15 & Chapter 8, pp. 279-308.*
Taggi, AE et al. "Generation of Ketenes from Acid Chlorides Using NaH/Crown Ether Shuttle-Deprotonation for Use in Asymmetric Catalysis." Organic Letters, vol. 4, No. 4, 2002, pp. 627-629.
International Search Report and Written Opinion, ISA/US, PCT/US16/55331, dated Dec. 8, 2016, 9 pages.

* cited by examiner

*Primary Examiner* — Patricia L Morris
(74) *Attorney, Agent, or Firm* — Faegre Baker Daniels LLP

(57) ABSTRACT

A process for the alkylation of picolinamides with substituted chloroacylals to produce a structure of Formula (III), wherein the reaction is performed in the presence of a phase-transfer catalyst and an inorganic halide co-catalyst.

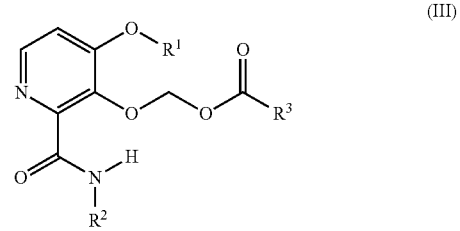

(III)

18 Claims, No Drawings

ALKYLATION OF PICOLINAMIDES WITH SUBSTITUTED CHLOROACYLALS UTILIZING A CROWN ETHER CATALYST

CROSS-REFERENCE TO RELATED APPLICATIONS

This application claims the benefit of U.S. Provisional Patent Application No. 62/237,844, filed Oct. 6, 2015, the disclosure of which is hereby incorporated by reference in its entirety.

FIELD

Aspect of the present disclosure relate to a process for the preparation of picolinamide derivatives. Some aspects of the present disclosure relate a process for the alkylation of hydroxypicolinamides with substituted chloroacylals utilizing a crown ether catalyst.

BACKGROUND AND SUMMARY

This patent application describes various routes used to prepare the fungicidal macrocyclic picolinamides. It may be advantageous to provide more direct and efficient methods for the preparation of the fungicidal macrocyclic picolinamides and related compounds, e.g., by the use of reagents and/or chemical intermediates that provide improved time and cost efficiency.

Provided herein are processes for the alkylation of picolinamides, including compounds of Formula (I):

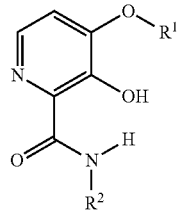

(I)

with a substituted chloroacylal of Formula (II):

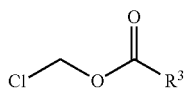

(II)

to produce a structure of Formula (III):

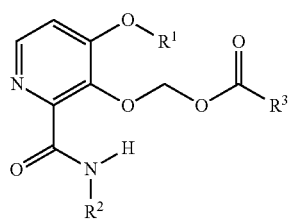

(III)

wherein: $R^1$ is a primary or secondary alkyl group;
$R^2$ is a heterocycle containing 5-12 atoms including 1-3 heteroatoms selected from the group consisting of N, O, P, and S with one or more substituents selected from the group consisting of $C_1$-$C_6$ alkyl, $C_1$-$C_6$ acyl, =O, benzyl, $C_1$-$C_6$ alkyl ether, or aryl ether; and
$R^3$ is a primary, secondary, or tertiary alkyl group.

In some exemplary embodiments, the picolinamide of Formula (I) is alkylated with the chloroacylal of Formula (II) in an organic solvent utilizing a crown ether phase-transfer catalyst, an inorganic iodide co-catalyst, and a metallic carbonate.

In one exemplary embodiment, the picolinamide is UK-2A (CAS No. 167173-85-5), (3S,6S,7R,8R)-8-benzyl-3-{[(3-hydroxy-4-methoxypyridin-2-yl)carbonyl]amino}-6-methyl-4,9-dioxo-1,5-dioxonan-7-yl 2-methylpropanoate], of the Formula (IV):

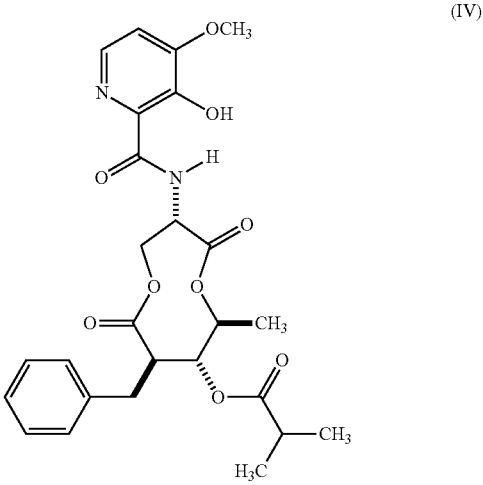

(IV)

In one exemplary embodiment, UK-2A is alkylated with chloromethyl isobutyrate (CAS No. 61644-18-6) of Formula (V):

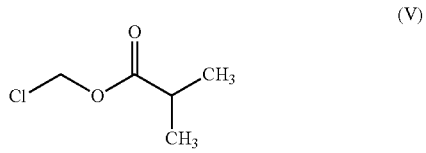

(V)

to form the structure of Formula (VI). Formula (VI) is (3S,6S,7R,8R)-8-benzyl-3-{[(4-methoxy-3-{[(2-methylpropanoyl)oxy]methoxy}-pyridin-2-yl)carbonyl]amino}-6-methyl-4,9-dioxo-1,5-dioxonan-7-yl 2-methylpropanoate]. Other by-products, such as the compound of Formula (VII), may also be formed. One advantage of the process disclosed herein is that it disfavors the formation of the compound of Formula (VII), thereby increasing the yield of the more desirable product of Formula (VI).

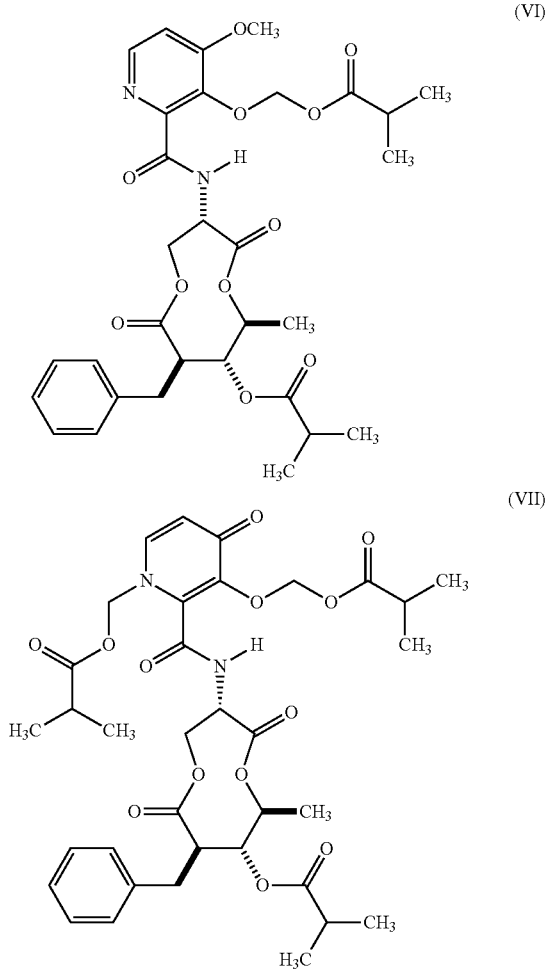

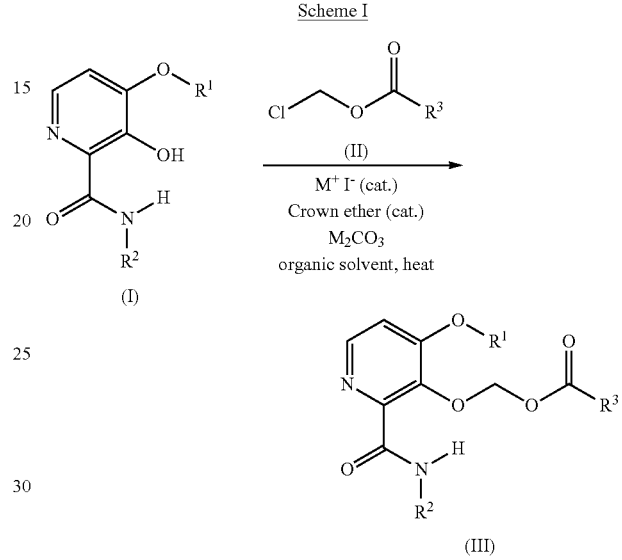

Throughout the disclosure, references to the compounds of the present disclosure are read as also including optical isomers and salts. Specifically, when compounds of the present disclosure contain a stereogenic carbon, it is understood that such compounds may include optical isomers, diastereomers and racemic and non-racemic mixtures thereof. Exemplary salts may include: Hydrochloride, hydrobromide, hydroiodide, and the like. Compounds containing carbon-carbon double bonds may be present as E, Z or E/Z mixtures.

Certain compounds disclosed in this document can exist as one or more isomer. It will be appreciated by those skilled in the art that one isomer may be more biologically active than the others. The structures described in the present disclosure are generally drawn in one geometric form representing the major stereoisomer present, and are not intended to represent all possible geometric and tautomeric forms of the molecule that may be present. In situations where the configuration of a particular stereogenic carbon atom is not known or is a mixture of similar amounts of each stereoisomer, the structure may be drawn without indication of the absolute configuration (i.e., no solid or dashed, wedge bond may be used).

The embodiments described above are intended merely to be exemplary, and those skilled in the art will recognize, or will be able to ascertain using no more than routine experimentation, numerous equivalents of specific processes, materials and procedures. All such equivalents are considered to be within the scope of the invention and are encompassed by the appended claims.

DETAILED DESCRIPTION

Picolinamides such as those of Formula (I) may be alkylated with a chloroacylal of Formula (II) to produce a structure according to Formula (III) according to Scheme I:

wherein $R^1$ is a primary or secondary alkyl group; $R^2$ is a heterocycle containing 5-12 atoms including 1-3 heteroatoms selected from the group consisting of N, O, P, and S with one or more substituents selected from the group consisting of $C_1$-$C_6$ alkyl, $C_1$-$C_6$ acyl, =O, benzyl, $C_1$-$C_6$ alkyl ether, or aryl ether; and $R^3$ is a primary, secondary, or tertiary alkyl group; and M is selected from the group consisting of lithium, sodium, or potassium. In addition to the compound of Formula (III), the reaction may also form one or more additional by-products.

In some embodiments, the reaction is carried out in an organic solvent. In some embodiments, the organic solvent is selected from the group consisting of ketonic, acetate ester, aromatic hydrocarbon, chlorinated organic, or organic nitrile. In still other embodiments, the organic solvent is selected from the group consisting of acetone, ethyl acetate, and toluene.

In some embodiments, the reaction is carried out in the presence of a phase-transfer catalyst and an inorganic halide co-catalyst. Some exemplary phase-transfer catalysts that may be used to practice the invention include, for example, crown ethers, Triton™ X-100, poly(ethylene glycol) having a molecular weight from about 200 to about 1000 Dalton, tris [2-(2-methoxyethoxy)ethyl]amine, 1-aza-15-crown-5,4,7,13,16,21-Pentaoxa-1,10-diazabicyclo-[8.8.5]tricosane (Kryptofix® 221), diethylene glycol dimethyl ether, triethylene glycol dimethyl ether, tetraethylene glycol dimethyl ether, tetra-n-butylammonium bromide, tetra-n-butylammonium iodide, tetramethylammonium chloride, and tetra-n-octylammonium bromide.

In some embodiments, the phase-transfer catalyst is a crown ether, and in still other embodiments, the phase-transfer catalyst is a crown ether oligomer of ethylene oxide. Exemplary crown ethers, that may be used to practice some aspects of the invention include for example 12-crown-4 (Formula VIII), 15-crown-5 (Formula IX), and 18-crown-6

(Formula X). Additional phase-transfer catalysts include benzo- and dibenzo-crown ethers thereof, such as benzo-12-crown-4 (Formula XI), benzo-15-crown-5 (Formula XII), and dibenzo-18-crown-6 (Formula XIII).

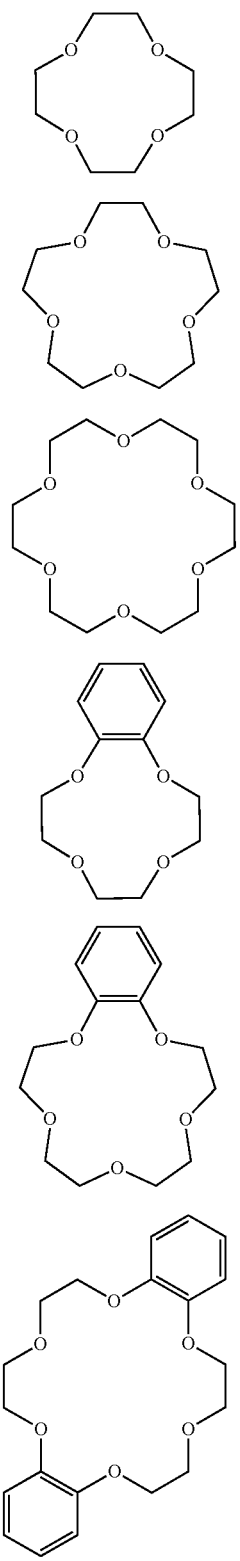

In some embodiments, the phase-transfer catalyst is provided in an amount as little as 1 mol %, as great as 2 mol %, 3 mol %, 5 mol % 7 mol %, 10 mol %, 15 mol %, or within any range defined between any two of the foregoing values, such as 1 mol % to 15 mol %.

Exemplary halide co-catalysts which may be used to practice some aspects of the invention include inorganic iodides, such as sodium iodide and potassium iodide. In some embodiments, the inorganic iodide co-catalyst is provided in an amount as little as 1 mol %, 2 mol %, 3 mol %, as great as 5 mol %, 8 mol %, 10 mol %, 15 mol % or within any range defined between any two of the foregoing values, such as 1 mol % to 15 mol %.

In some embodiments, the reaction is carried out in a basic environment. Bases which may be used to practice aspects of the invention include metal carbonates, such as sodium carbonate ($Na_2CO_3$) and potassium carbonate ($K_2CO_3$). In one embodiment, the metal carbonate is provided in an amount, based on 1.0 molar equivalent of the picolinamide of Formula (I), as little as 0.9 equivalents, 1 equivalents, 1.25 equivalents as great as 1.5 equivalents, 2 equivalents, 2.5 equivalents, or within any range defined between any two of the foregoing values, such as 0.9 equivalents to 2.5 equivalents. In a more particular embodiment, a stoichiometric amount of potassium carbonate or sodium carbonate is provided.

In some embodiments of the invention, the substituted chloroacylal of Formula (II) is provided in an amount, based on 1.0 molar equivalent of the picolinamide of Formula (I), as little as 0.9 equivalents, 1.0 equivalents as great as 1.1 equivalents, 1.2 equivalents, 1.3 equivalents, 1.4 equivalents, or 1.5 equivalents, or within any range defined between any two of the foregoing values, such as 0.9 equivalents to 1.5 equivalents. In still other embodiments, a stoichiometric amount of the substituted chloroacylal is provided.

In some embodiments, the reaction is conducted at a temperature as low as 30° C., 40° C., 50° C., as high as 100° C., 110° C., or within any range defined between any two of the foregoing values, such as 30° C. to 110° C.

In some embodiments, the wt % of the picolinamide of Formula (I) in the reaction is as little as 1 wt %, 5 wt %, 8 wt %, 10 wt %, as great as 15 wt %, 20 wt %, 25 wt %, or within any range defined between any two of the foregoing values, such as 1 wt % to 25 wt %, based on the total mass of the reaction mixture.

In some embodiments, the picolinamide of Formula (I) is UK-2A, the substituted chloroacylal of Formula (II) is chloromethyl isobutyrate of Formula (V), the metallic carbonate is sodium carbonate ($Na_2CO_3$), and the compound of Formula (III) is (3S,6S,7R,8R)-8-benzyl-3-{[(4-methoxy-3-{[(2-methylpropanoyl)oxy]methoxyl}-pyridin-2-yl)carbonyl]amino}-6-methyl-4,9-dioxo-1,5-dioxonan-7-yl 2-methylpropanoate] (Formula VI) according to Scheme II.

Scheme II

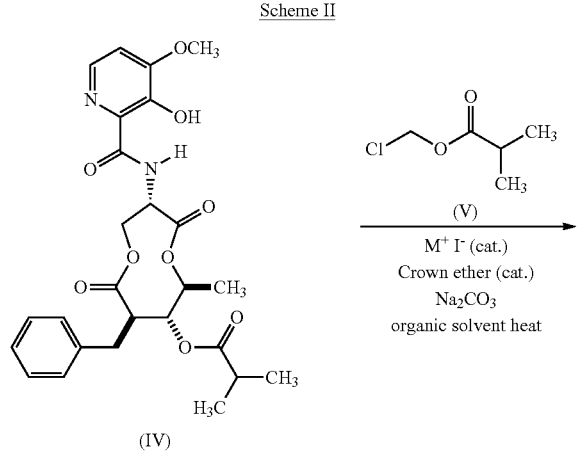

(IV)

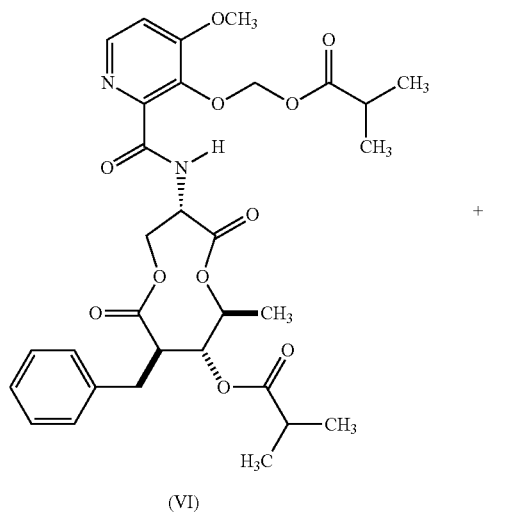

(VI)

+

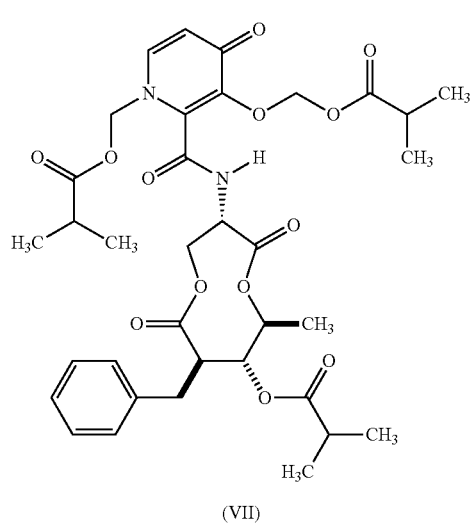

(VII)

As shown in Scheme II, the reaction may produce additional byproducts, such as the compound of Formula (VII). In one exemplary embodiment, the reaction has a relatively high selectivity for the compound of Formula (VI) when a crown ether catalyst is used. In one exemplary embodiment, the yield of the compound of Formula (VI) is as little as about 80±2% or as great as about 98±2% or any value within the range defined by the foregoing values.

EXAMPLES

As shown in Table 1, the use of a crown ether phase-transfer catalyst in the production of compounds such as those of Formula (VI) from starting materials such as picolinamides has a beneficial impact on both reaction rate and the yield of the compound of Formula (VI). The absence of a crown ether catalyst (Table 1, Entry 1) in the reaction provides a modest yield of the compound of Formula (VI) (88%) and the reaction requires 48 h to reach a conversion of the compound of Formula (IV) of 94%. The presence of 15-crown-5 (Formula IX) as a phase-transfer catalyst in the reaction provides >99% conversion of the compound of Formula (IV) within 24 h and a 95% yield of the compound of Formula (VI) and a 5% yield of the by-product of Formula (VII) (Table 1, Entry 2). A reduction in the loading of 15-crown-5 (Formula IX) reduces the yield of the compound of Formula (VI) from 95% to 93% and increases the yield of the by-product of Formula (VII) from 5% to 6% (Table 1, Entry 3 versus Entry 2). An increase in the loading of 15-crown-5 (Formula IX) improves the conversion of the compound of Formula (IV) (>99% within 10 h) and results in an increase in the yield of the compound of Formula (VI) from 95% to 97% and a decrease in the yield of the by-product of Formula (VII) from 5% to 3% (Table 1, Entry 4 versus Entry 2). High yield (>96%) of the compound of Formula VI can also be achieved at different loadings of the sodium iodide co-catalyst (Table 1, Entries 5-7). In comparison to 15-crown-5, phase-transfer catalyst systems utilizing benzo-15-crown-5 (Formula XII) with sodium iodide (Table 1, Entry 8) or 18-crown-6 (Formula X) with potassium iodide (Table 1, Entry 9) also provide a yield of the compound of Formula (VI) that is superior to the yield of the compound of Formula (VI) in the absence of a phase-transfer catalyst (cf. Table 1, Entry 1). Alternatively, the solvents acetone (Table 1, Entry 10) and toluene (Table 1, Entry 11) can be used in place of ethyl acetate while maintaining a high yield of the compound of Formula (VI) provided that the reaction is carried out in the presence of at least one crown ether catalyst. In still other experiments, in the absence of a phase-transfer catalyst reactions with the solvents acetone or toluene exhibited a >5% reduction in the conversion of Formula (IV) to product and the yield of Formula (VI) relative to similar reactions carried out in the presence of a crown ether catalyst.

TABLE 1

Comparison of Various Reaction Conditions.

| Entry | Solvent | Temp (° C.) | Iodide (mol %) | Crown ether (mol %) | Conversion of IV @ Time (h) | | | | | VI (%) | VII (%) |
|---|---|---|---|---|---|---|---|---|---|---|---|
| | | | | | 5 h | 10 h | 24 h | 30 h | 48 h | | |
| 1 | Ethyl acetate | 55 | NaI (6) | None (0) | 18 | 33 | 70 | — | 94 | 88 | 5 |
| 2 | Ethyl acetate | 55 | NaI (6) | IX (6) | 68 | 93 | >99 | — | — | 95 | 5 |
| 3 | Ethyl acetate | 65 | NaI (6) | IX (2) | 54 | 86 | >99 | — | — | 93 | 6 |
| 4 | Ethyl acetate | 65 | NaI (6) | IX (10) | 89 | >99 | — | — | — | 97 | 3 |
| 5 | Ethyl acetate | 45 | NaI (6) | IX (10) | 49 | 92 | >99 | — | — | 97 | 2 |
| 6 | Ethyl acetate | 55 | NaI (9) | IX (10) | 86 | >99 | — | — | — | 96 | 4 |
| 7 | Ethyl acetate | 55 | NaI (3) | IX (10) | 61 | 86 | >99 | — | — | 96 | 2 |
| 8 | Ethyl acetate | 55 | NaI (6) | XII (5) | 50 | 85 | >99 | — | — | 95 | 5 |
| 9 | Ethyl acetate | 55 | KI (6) | X (6) | 57 | 92 | >99 | — | — | 91 | 4 |
| 10 | Acetone | 54 | NaI (6) | IX (6) | 77 | 97 | >99 | — | — | 92 | 4 |
| 11 | Toluene | 55 | NaI (6) | IX (6) | 20 | 43 | 96 | 99 | — | 95 | 3 |

Example 1

Conversion of UK-2A (Formula IV) to Formula (VI) in the Presence of Chloromethyl Isobutyrate (Formula V), 15-crown-5 (Formula IX), Sodium Iodide (NaI), and Sodium Carbonate ($Na_2CO_3$) in Ethyl Acetate Solvent (Corresponding to Entry 4 of Table 1)

A 1-L jacketed glass reactor equipped with a nitrogen pad, overhead stirrer motor, down-pumping 45° pitched 4-blade impeller, "h" baffle, West condenser, and thermowell was charged sequentially with solid UK-2A (56.10 g, 0.109 mol, 1.0 equiv), anhydrous $Na_2CO_3$ (23.09 g, 0.218 mol, 2.0 equiv), solid NaI (0.979 g, 0.0065 mol, 6 mol %), nonyl phenyl ketone (1.5022 g, nonreactive internal standard for HPLC analysis), 15-crown-5 (2.444 g, 0.0109 mol, 10 mol %), neat chloromethyl isobutyrate (16.47 g, 0.120 mol, 1.1 equiv), and ethyl acetate (361 g). The 1-L reactor was placed under an atmosphere of nitrogen, agitation was initiated, and the reaction mixture was heated to 65° C. Samples of the reaction mixture (approximately 1 mL) were removed at 5 h and 10 h. Each sample was added to fresh ethyl acetate (5 mL), syringe filtered, and diluted approximately 6:1 (v/v) with 0.1% formic acid in N,N-dimethylformamide. The resulting samples were analyzed by HPLC (UV detection, 270 nm) and the molar concentrations of unreacted UK-2A (Formula IV), Formula (VI), and the by-product of Formula (VII) were determined based on the known quantity of internal standard (nonyl phenyl ketone). The conversion of Formula (IV) and the yields of Formula (VI) and Formula (VII) could be calculated on the basis of this information (see for example Entry 4 of Table 1).

Example 2

Conversion of UK-2A (Formula IV) to Formula (VI) in the Presence of Chloromethyl Isobutyrate (Formula V), benzo-15-crown-5 (Formula XII), Sodium Iodide (NaI), and Sodium Carbonate ($Na_2CO_3$) in Ethyl Acetate Solvent (Corresponding to Entry 8 of Table 1)

A 1-L jacketed glass reactor equipped with a nitrogen pad, overhead stirrer motor, down-pumping 45° pitched 4-blade impeller, "h" baffle, West condenser, and thermowell was charged sequentially with solid UK-2A (56.09 g, 0.109 mol, 1.0 equiv), anhydrous $Na_2CO_3$ (23.09 g, 0.218 mol, 2.0 equiv), solid NaI (0.973 g, 0.0065 mol, 6 mol %), nonyl phenyl ketone (1.5269 g, nonreactive internal standard for HPLC analysis), benzo-15-crown-5 (1.454 g, 0.0054 mol, 5 mol %), neat chloromethyl isobutyrate (16.48 g, 0.120 mol, 1.1 equiv), and ethyl acetate (317 g). The 1-L reactor was placed under an atmosphere of nitrogen, agitation was initiated, and the reaction mixture was heated to 55° C. Samples of the reaction mixture (approximately 1 mL) were removed at 5 h, 10 h, and 24 h. Each sample was added to fresh ethyl acetate (5 mL), syringe filtered, and diluted approximately 6:1 (v/v) with 0.1% formic acid in N,N-dimethylformamide. The resulting samples were analyzed by HPLC (UV detection, 270 nm) and the molar concentrations of unreacted UK-2A (Formula IV), Formula (VI), and the by-product of Formula (VII) were determined based on the known quantity of internal standard (nonyl phenyl ketone). The conversion of Formula (IV) and the yields of Formula (VI) and Formula (VII) could be calculated on the basis of this information (see for example, Entry 8 of Table 1).

Example 3

Conversion of UK-2A (Formula IV) to Formula (VI) in the Presence of Chloromethyl Isobutyrate (Formula V), 18-crown-6 (Formula X), Potassium Iodide (KI), and Sodium Carbonate (Na$_2$CO$_3$) in Ethyl Acetate Solvent (Corresponding to Entry 9 of Table 1)

A 1-L jacketed glass reactor equipped with a nitrogen pad, overhead stirrer motor, down-pumping 45° pitched 4-blade impeller, "h" baffle, West condenser, and thermowell was charged sequentially with solid UK-2A (56.05 g, 0.109 mol, 1.0 equiv), anhydrous Na$_2$CO$_3$ (23.12 g, 0.218 mol, 2.0 equiv), solid KI (1.096 g, 0.0065 mol, 6 mol %), nonyl phenyl ketone (1.5270 g, nonreactive internal standard for HPLC analysis), 18-crown-6 (1.454 g, 0.0066 mol, 6 mol %), neat chloromethyl isobutyrate (16.54 g, 0.121 mol, 1.1 equiv), and ethyl acetate (317 g). The 1-L reactor was placed under an atmosphere of nitrogen, agitation was initiated, and the reaction mixture was heated to 55° C. Samples of the reaction mixture (approximately 1 mL) were removed at 5 h, 10 h, and 24 h. Each sample was added to fresh ethyl acetate (5 mL), syringe filtered, and diluted approximately 6:1 (v/v) with 0.1% formic acid in N,N-dimethylformamide. The resulting samples were analyzed by HPLC (UV detection, 270 nm) and the molar concentrations of unreacted UK-2A (Formula IV), Formula (VI), and the by-product of Formula (VII) were determined based on the known quantity of internal standard (nonyl phenyl ketone). The conversion of Formula (IV) and the yields of Formula (VI) and Formula (VII) could be calculated on the basis of this information (see for example, Entry 9 of Table 1).

Example 4

Conversion of UK-2A (Formula IV) to Formula (VI) in the Presence of Chloromethyl Isobutyrate (Formula V), 15-crown-5 (Formula X), Sodium Iodide (NaI), and Sodium Carbonate (Na$_2$CO$_3$) in Acetone Solvent (Corresponding to Entry 10 of Table 1)

A 1-L jacketed glass reactor equipped with a nitrogen pad, overhead stirrer motor, down-pumping 45° pitched 4-blade impeller, "h" baffle, West condenser, and thermowell was charged sequentially with solid UK-2A (56.02 g, 0.109 mol, 1.0 equiv), anhydrous Na$_2$CO$_3$ (23.09 g, 0.218 mol, 2.0 equiv), solid NaI (0.971 g, 0.0065 mol, 6 mol %), nonyl phenyl ketone (1.5469 g, nonreactive internal standard for HPLC analysis), 15-crown-5 (1.467 g, 0.0065 mol, 6 mol %), neat chloromethyl isobutyrate (16.50 g, 0.120 mol, 1.1 equiv), and acetone (317 g). The 1-L reactor was placed under an atmosphere of nitrogen, agitation was initiated, and the reaction mixture was heated to reflux (approximately 54° C.). Samples of the reaction mixture (approximately 1 mL) were removed at 5 h, 10 h, and 24 h. Each sample was added to fresh ethyl acetate (5 mL), syringe filtered, and diluted approximately 6:1 (v/v) with 0.1% formic acid in N,N-dimethylformamide. The resulting samples were analyzed by HPLC (UV detection, 270 nm) and the molar concentrations of unreacted UK-2A (Formula IV), Formula (VI), and the by-product of Formula (VII) were determined based on the known quantity of internal standard (nonyl phenyl ketone). The conversion of Formula (IV) and the yields of Formula (VI) and Formula (VII) could be calculated on the basis of this information (see for example Entry 10 of Table 1).

Example 5

Conversion of UK-2A (Formula IV) to Formula (VI) in the Presence of Chloromethyl Isobutyrate (Formula V), 15-crown-5 (Formula X), Sodium Iodide (NaI), and Sodium Carbonate (Na$_2$CO$_3$) in Toluene Solvent (Corresponding to Entry 11 of Table 1)

A 1-L jacketed glass reactor equipped with a nitrogen pad, overhead stirrer motor, down-pumping 45° pitched 4-blade impeller, "h" baffle, West condenser, and thermowell was charged sequentially with solid UK-2A (56.16 g, 0.109 mol, 1.0 equiv), anhydrous Na$_2$CO$_3$ (23.12 g, 0.218 mol, 2.0 equiv), solid NaI (0.961 g, 0.0064 mol, 6 mol %), nonyl phenyl ketone (1.5049 g, nonreactive internal standard for HPLC analysis), 15-crown-5 (1.481 g, 0.0066 mol, 6 mol %), neat chloromethyl isobutyrate (16.53 g, 0.121 mol, 1.1 equiv), and toluene (326 g). The 1-L reactor was placed under an atmosphere of nitrogen, agitation was initiated, and the reaction mixture was heated to 55° C. Samples of the reaction mixture (approximately 1 mL) were removed at 5 h, 10 h, 24 h, and 30 h. Each sample was added to fresh ethyl acetate (5 mL), syringe filtered, and diluted approximately 6:1 (v/v) with 0.1% formic acid in N,N-dimethylformamide. The resulting samples were analyzed by HPLC (UV detection, 270 nm) and the molar concentrations of unreacted UK-2A (Formula IV), Formula (VI), and the by-product of Formula (VII) were determined based on the known quantity of internal standard (nonyl phenyl ketone). The conversion of Formula (IV) and the yields of Formula (VI) and Formula (VII) could be calculated on the basis of this information (see for example, Entry 11 of Table 1).

What is claimed is:

1. A method, comprising the steps of:

reacting a picolinamide of Formula (I):

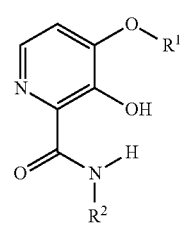

with a substituted chloroacylal of Formula (II):

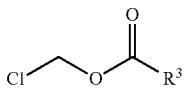

to produce a compound of Formula (III):

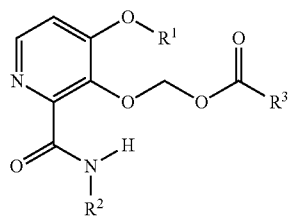

(III)

wherein:
the picolinamide of Formula (I) is (3S,6S,7R,8R)-8-benzyl-3-{[(3-hydroxy-4-methoxypyri-2-yl)carbonyl]amino}-6-methyl-4,9-dioxo-1,5-dioxonan-7-yl 2-methylpropanoate], the substituted chloroacylal of Formula (II) is chloromethyl isobutyrate, and the compound of Formula (III) is (3S,6S,7R,8R)-8-benzyl-3-{[(4-methoxy-3-{[(2-methylpropanoyl)oxy]methoxy}-pyridin-2-yl)carbonyl]amino}-6-methyl-4,9-diox-1,5-dioxonan-7-yl 2-methylpropanoate]; and
wherein the reacting step is conducted in the presence of a crown ether and an inorganic halide co-catalyst, wherein the crown ether is at least one ether selected from the group consisting of: 12-crown-4, 15-crown-5, 18-crown-6, and benzo- and dibenzo-crown ethers thereof.

2. The method of claim 1, wherein the crown ether is at least one ether selected from the group consisting of: 12-crown-4, 15-crown-5, 18-crown-6, benzo-12-crown-4, benzo-15-crown-5, and dibenzo-18-cown-6.

3. The method of claim 1, wherein the crown ether is at least one ether selected from the group consisting of: 15-crown-5, 18-crown-6, and benzo-15-crown-5.

4. The method of claim 1, wherein the inorganic halide co-catalyst is an inorganic iodide.

5. The method of claim 4, wherein the inorganic iodide is at least one iodide salt selected from the group consisting of sodium iodide and potassium iodide.

6. The method of claim 1, wherein the reaction is carried out in an organic solvent.

7. The method of claim 6, wherein the organic solvent is at least one organic solvent selected from the group consisting of ketonic, acetate ester, aromatic hydrocarbon, chlorinated organic, and organic nitrile.

8. The method of claim 7, wherein the organic solvent is at least one solvent selected from the group consisting of acetone, ethyl acetate, and toluene.

9. The method of claim 1, wherein the reaction is carried out in a basic environment.

10. The method of claim 9, wherein the basic environment is provided by a metallic carbonate.

11. The method of claim 10, wherein the metal carbonate is at least one carbonate selected from the group consisting of sodium carbonate and potassium carbonate.

12. A method comprising:
reacting (3S,6S,7R,8R)-8-benzyl-3-{[(3-hydroxy-4-methoxypyridin-2-yl)carbonyl]-amino}-6-methyl-4,9-dioxo-1,5-dioxonan-7-yl 2-methylpropanoate] with chloromethyl isobutyrate in the presence of a crown ether and an inorganic iodide to produce (3S,6S,7R,8R)-8-benzyl-3-{[(4-methoxy-3-{[(2-methylpropanoyl)oxy]methoxy}-pyridin-2-yl)carbonyl]amino}-6-methyl-4,9-dioxo-1,5-dioxonan-7-yl
2-methylpropanoate] and one or more by-products, wherein the crown ether is at least one ether selected from the group consisting of: 12-crown-4, 15-crown-5, 18-crown-6, and benzo- and dibenzo-crown ethers thereof.

13. The method of claim 12, wherein the one or more by-products is a compound of Formula VII:

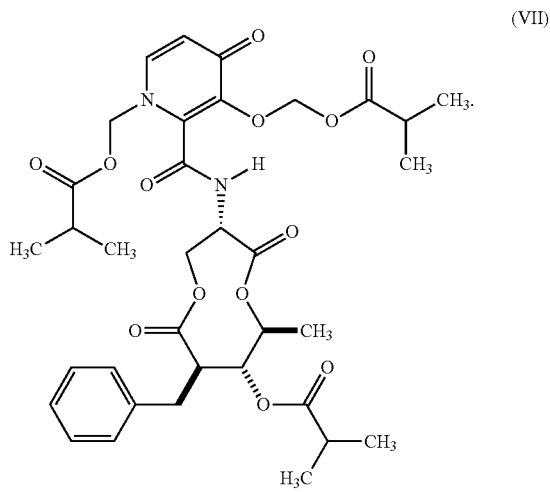 [SMILES: CC(C)C(=O)OCOc1c(C(=O)N[C@H]2COC(=O)[C@H](Cc3ccccc3)[C@@H](OC(=O)C(C)C)[C@H](C)OC2=O)n(COC(=O)C(C)C)ccc1=O]

(VII)

14. The method of claim 12, wherein the yield of (3S,6S,7R,8R)-8-benzyl-3-{[(4-methoxy-3-{[(2-methylpropanoyl)oxy]methoxy}-pyridin-2-yl)carbonyl]amino}-6-methyl-4,9-dioxo-1,5-dioxonan-7-yl 2-methylpropanoate] is about 80% (±2%) or greater.

15. The method of claim 12, wherein the crown ether is at least one ether selected from the group consisting of: 12-crown-4, 15-crown-5, 18-crown-6, benzo-12-crown-4, benzo-15-crown-5, and dibenzo-18-cown-6.

16. The method of claim 12, wherein the inorganic iodide is at least one iodide selected from the group consisting of sodium iodide and potassium iodide.

17. The method of claim 12, wherein the reaction is carried out in at least one organic solvent selected from the group consisting of acetone, ethyl acetate, and toluene.

18. The method of claim 12, wherein the crown ether is at least one ether selected from the group consisting of: 15-crown-5, 18-crown-6, and benzo-15-crown-5.

* * * * *